United States Patent

Hirt et al.

Patent Number: 5,454,800
Date of Patent: Oct. 3, 1995

[54] ABSORBENT ARTICLE

[75] Inventors: Dede A. Hirt, Appleton; Valerie V. Finch, Neenah; Laurie Couture-Dorschner, Hortonville, all of Wis.

[73] Assignee: Kimberly-Clark Corporation, Neenah, Wis.

[21] Appl. No.: 58,249

[22] Filed: May 12, 1993

[51] Int. Cl.⁶ .......................... A61F 13/15; A61F 13/20
[52] U.S. Cl. ...................... 604/378; 604/358; 604/385.1
[58] Field of Search ........................ 604/358, 361–362, 604/374, 378–385.1

[56] References Cited

U.S. PATENT DOCUMENTS

| | | |
|---|---|---|
| 1,863,333 | 12/1929 | Heitmeyer . |
| 1,910,872 | 5/1933 | Williams . |
| 2,047,054 | 7/1936 | Beyer, Jr. et al. . |
| 2,564,689 | 8/1951 | Harwood et al. . |
| 2,772,678 | 12/1956 | Leupold . |
| 2,787,271 | 4/1957 | Clark . |
| 2,900,980 | 8/1959 | Harwood . |
| 3,073,308 | 1/1963 | Stamberger . |
| 3,088,463 | 5/1963 | Harmon . |
| 3,343,543 | 9/1967 | Glassman . |
| 3,344,789 | 10/1967 | Arnold et al. . |
| 3,375,827 | 4/1968 | Bletzinger et al. . |
| 3,397,697 | 8/1968 | Rickard . |
| 3,403,681 | 10/1968 | Hoey et al. . |
| 3,525,337 | 8/1970 | Simons et al. . |
| 3,545,442 | 9/1970 | Wicker et al. . |
| 3,654,060 | 4/1972 | Goldman . |
| 3,654,929 | 4/1972 | Nilsson et al. . |
| 3,667,468 | 6/1972 | Nystrand et al. . |
| 3,699,966 | 10/1972 | Chapuis . |
| 3,746,592 | 7/1973 | Nystrand et al. . |
| 3,771,525 | 11/1973 | Chapuis . |
| 3,865,112 | 2/1975 | Roeder . |
| 3,886,941 | 6/1975 | Duane et al. . |
| 3,929,135 | 12/1975 | Thompson . |
| 3,939,838 | 2/1976 | Fujinami et al. . |
| 3,945,386 | 3/1976 | Anczurowski et al. . |
| 3,954,107 | 5/1976 | Chesky et al. . |
| 3,965,906 | 6/1976 | Karami . |
| 3,967,623 | 7/1976 | Butterworth et al. . |
| 3,994,299 | 11/1976 | Karami . |
| 4,014,341 | 3/1977 | Karami . |
| 4,029,101 | 6/1977 | Chesky et al. . |

(List continued on next page.)

FOREIGN PATENT DOCUMENTS

| | | |
|---|---|---|
| 0272683A2 | 6/1988 | European Pat. Off. . |
| 0234194B1 | 11/1992 | European Pat. Off. . |
| 122727 | 8/1989 | Japan . |
| 168950 | 6/1990 | Japan . |
| 1333081 | 10/1973 | United Kingdom . |
| 2124907 | 2/1984 | United Kingdom . |
| 2165757 | 4/1986 | United Kingdom ................ 604/358 |
| 2180162 | 3/1987 | United Kingdom . |
| 2258840 | 2/1993 | United Kingdom . |
| 2258404 | 2/1993 | United Kingdom . |
| WO91/00719 | 1/1991 | WIPO . |
| WO91/11163 | 8/1991 | WIPO . |

*Primary Examiner*—Randall L. Green
*Assistant Examiner*—P. Zuttarelli
*Attorney, Agent, or Firm*—Thomas J. Connelly

[57] ABSTRACT

An absorbent article is disclosed for absorbing body fluids such as urine, menses, blood, excrement, etc. The absorbent article includes a liquid-permeable cover, a liquid-impermeable baffle and an absorbent positioned therebetween. The absorbent is constructed of first and second members each having a predetermined width, with the width of the first member being equal to or greater than the width of the second member. The second member is positioned below at least a portion of the first member. The second member has a greater wicking capability than said first member and this facilitates movement of body fluid in a horizontal plane throughout the second member. The body fluid present in the second member will then be transferred back into the first member over an area equal to the saturated area of the second member.

30 Claims, 3 Drawing Sheets

U.S. PATENT DOCUMENTS

| | | | |
|---|---|---|---|
| 4,037,602 | 7/1977 | Hawthorne | 604/385.1 |
| 4,057,061 | 11/1977 | Ishikawa et al. . | |
| 4,069,822 | 1/1978 | Buell . | |
| 4,079,739 | 3/1978 | Whitehead . | |
| 4,100,324 | 7/1978 | Anderson et al. . | |
| 4,195,634 | 4/1980 | DiSalvo et al. . | |
| 4,223,677 | 8/1980 | Anderson . | |
| 4,232,674 | 11/1980 | Melican | 604/369 |
| 4,285,343 | 8/1981 | McNair . | |
| 4,323,068 | 4/1982 | Aziz . | |
| 4,323,069 | 4/1982 | Ahr et al. . | |
| 4,324,246 | 4/1982 | Mullane et al. . | |
| 4,327,731 | 5/1982 | Powell . | |
| 4,357,939 | 11/1982 | Jackson et al. . | |
| 4,372,312 | 2/1983 | Fendler et al. . | |
| 4,397,644 | 8/1983 | Matthews et al. . | |
| 4,411,660 | 10/1983 | Dawn et al. . | |
| 4,433,972 | 2/1984 | Malfitano . | |
| 4,507,121 | 3/1985 | Leung . | |
| 4,540,414 | 9/1985 | Wishman . | |
| 4,551,142 | 11/1985 | Kopolow . | |
| 4,589,876 | 5/1986 | Van Tilburg . | |
| 4,608,047 | 8/1986 | Mattingly . | |
| 4,623,340 | 11/1986 | Luceri . | |
| 4,626,254 | 12/1986 | Widlund et al. . | |
| 4,627,848 | 12/1986 | Lassen et al. . | |
| 4,629,643 | 12/1986 | Curro et al. . | |
| 4,631,062 | 12/1986 | Lassen et al. . | |
| 4,636,209 | 1/1987 | Lassen | 604/378 |
| 4,676,786 | 6/1987 | Nishino . | |
| 4,687,478 | 8/1987 | Van Tilburg . | |
| 4,690,679 | 9/1987 | Mattingly, III et al. . | |
| 4,705,513 | 11/1987 | Sheldon et al. . | |
| 4,710,186 | 12/1987 | DeRossett et al. . | |
| 4,731,071 | 3/1988 | Pigneul . | |
| 4,738,674 | 4/1988 | Todd et al. . | |
| 4,741,941 | 5/1988 | Englebert et al. . | |
| 4,755,413 | 7/1988 | Morris . | |
| 4,773,905 | 9/1988 | Molee et al. . | |
| 4,798,601 | 1/1989 | Shirose et al. . | |
| 4,798,603 | 1/1989 | Meyer et al. . | |
| 4,798,604 | 1/1989 | Carter . | |
| 4,806,411 | 2/1989 | Mattingly, III et al. . | |
| 4,822,668 | 4/1989 | Tanaka et al. . | |
| 4,846,813 | 7/1989 | Raley . | |
| 4,846,824 | 7/1989 | Lassen et al. . | |
| 4,880,419 | 11/1989 | Ness . | |
| 4,886,632 | 12/1989 | Van Iten et al. . | |
| 4,895,749 | 1/1990 | Rose . | |
| 4,908,026 | 3/1990 | Sukiennik et al. . | |
| 4,950,264 | 8/1990 | Osborn, III . | |
| 4,963,139 | 10/1990 | Dabroski . | |
| 4,973,325 | 11/1990 | Sherrod et al. . | |
| 4,988,344 | 1/1991 | Reising et al. . | |
| 5,009,653 | 4/1991 | Osborn, III . | |
| 5,037,409 | 8/1991 | Chen et al. . | |
| 5,037,412 | 8/1991 | Tanzer et al. . | |
| 5,125,918 | 6/1992 | Seidy . | |
| 5,135,521 | 8/1992 | Luceri et al. . | |
| 5,188,625 | 4/1993 | Van Iten et al. . | |
| 5,201,727 | 4/1993 | Nakanishi et al. . | |
| 5,219,341 | 6/1993 | Serbiak et al. | 604/361 |
| 5,257,982 | 11/1993 | Cohen et al. | 604/358 |

ABSORBENT ARTICLE

FIELD OF THE INVENTION

This invention relates to an absorbent article for absorbing body fluid. More particularly, this invention relates to an absorbent article, such as a sanitary napkin, which provides a post-use visual signal to the user that the body fluid is staying in the center of the article.

BACKGROUND OF THE INVENTION

An absorbent article refers to products such as diapers, sanitary napkins, training pants, incontinent garments, overnight pads, panty liners, underarm shields. Such articles are designed to absorb body fluid, such as urine, menses, blood, perspiration, and other excrements discharged by a body. Sanitary napkins, also referred to as catamenial pads, feminine pads, overnight pads, panty liners and panty shields are designed to be worn by a female to absorb menses and other body fluids discharged before, during and after a menstrual period. Such products are external devices which are generally held in position by a garment attachment adhesive or by a mechanical attachment to an adjacent undergarment. Such articles differ from tampons which are classified as internal devices and which are designed to be physically inserted into a woman's vagina.

Today, there is a move by manufacturers to make external sanitary products thinner than in the past so that they are more discrete while delivering an equal amount of fluid capacity as the thicker products. This evolution has seen a decrease in thickness of sanitary products from about 25 millimeters (mm), down to about 10 mm, and even down to a thickness of less than 5 mm. The primary reason for the reduction in thickness has been the use of new superabsorbent materials. However, superabsorbent materials are very expensive and can cause gel blocking as they swell up with fluid. Because of this, there is a desire to construct an absorbent article, especially a thin article, which has adequate fluid capacity and rapid fluid intake while using a lesser amount of superabsorbent or by eliminating superabsorbents altogether. This will substantially reduce the cost of manufacturing such an article.

It is also desirable to construct an absorbent article which can deliver a post-use visual signal to the user that the body fluid is staying in the center of the article. If the fluid stain approaches the side edges of the absorbent article, the user could clearly see that the article needs to be changed.

Another important aspect of absorbent articles is their ability to wick menses. Menses is very viscous and can contain small particles of body tissue which tend to cling to the cover and can restrict the passage of additional body fluid into the absorbent article. Manufacturers of absorbent articles are always on the lookout for a new material or arrangement of layers which will provide improved wicking capabilities.

Now an absorbent article has been invented which utilizes an absorbent having a high wicking capability, especially for menses, as well as providing a post-use visual signal to the user that the body fluid is staying in the center of the article.

SUMMARY OF THE INVENTION

Briefly, this invention relates to an absorbent article for absorbing body fluids such as urine, menses, blood, excrement, etc. The absorbent article includes a liquid-permeable cover, a liquid-impermeable baffle and an absorbent positioned therebetween. The absorbent is constructed of first and second members each having a predetermined width, with the width of the first member being equal to or greater than the width of the second member. The second member is positioned below at least a portion of the first member. The second member has a greater wicking capability than said first member to facilitate movement of body fluid in a horizontal plane throughout the second member. This wicking capability can be expressed as a ratio of length of a fluid stain in the second member to length of a fluid stain in the first member being greater than 1.7 when the length of the fluid stain in the second member is at least 76 mm. Body fluid present in the second member will then be transferred back into the first member over an area equal to the saturate area of the second member. As the absorbent article becomes saturated with body fluid which is retained in an area corresponding to the surface area of the second member, the user receives a post-use visual signal that the fluid is staying in the center of the article.

The general object of this invention is to provide an absorbent article for absorbing body fluids such as urine, menses, blood, excrement, etc. A more specific object of this invention is to provide an absorbent article, such as a sanitary napkin, which provides a post-use visual signal to the user that the fluid is staying in the center of the article.

Another object of this invention is to provide an absorbent article for absorbing body fluid which has improved wicking capabilities expressed by a ratio of length of a fluid stain in a member having a high wicking capability to length of a fluid stain in another member having a lower wicking capability than the high wicking member, the ratio being at least 1.7 when the length of the fluid stain in the high wicking member is at least 76 mm.

A further object of this invention is to provide an absorbent article having stain masking properties in that the fluid stain in the first absorbent member is less severe than the fluid stain in the second absorbent member.

Still another object of this invention is to provide an absorbent article which is less than 5 mm thick and which is easy to manufacture and low in cost.

Other objects and advantages of the present invention will become more apparent to those skilled in the art in view of the following description and the accompanying drawings.

DETAILED DESCRIPTION OF THE PREFERRED EMBODIMENTS

Figure 1:
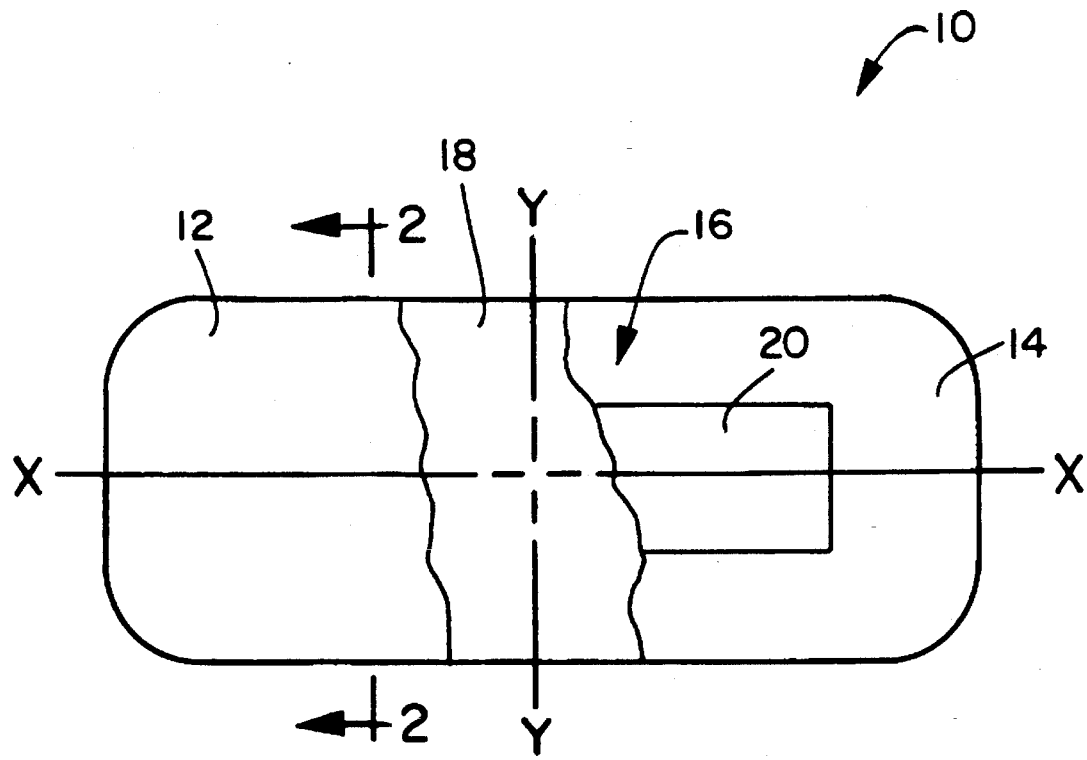
FIG. 1 is a top view of an absorbent article partially cut away to reveal the interior members.
Figure 2:
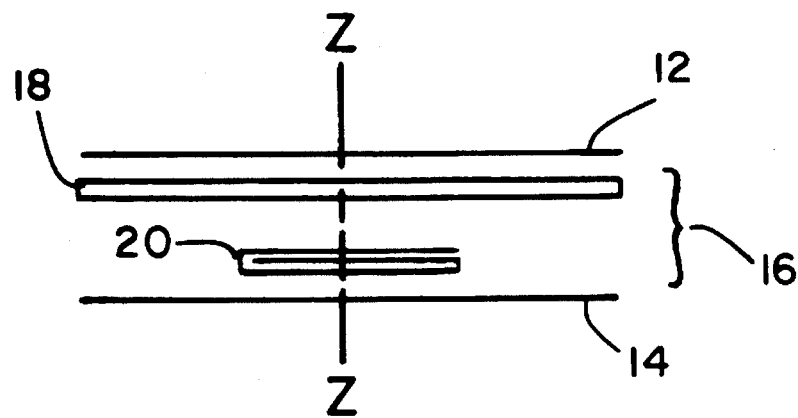
FIG. 2 is a cross-sectional view of FIG. 1 taken along line 2—2.

Referring to FIGS. 1 and 2, an absorbent article 10 is shown which is capable of absorbing body fluid. The thickness of the absorbent article 10 should be less than 25 mm, preferably, less than 10 mm, and most preferably, between about 2 mm to about 5 mm. For an ultra thin absorbent article, the thickness should be less than about 5 mm. The absorbent article 10 can be a diaper, a training pant, a sanitary napkin, a panty liner, an overnight pad, an incontinent garment, an underarm shield or any other known disposable product capable of absorbing urine, menses, blood, perspiration, excrement, or other fluid discharged by a human body. For the purpose of discussion, the absorbent article 10 will be described in terms of a sanitary napkin.

The absorbent article 10 includes a liquid-permeable cover 12, a liquid-impermeable baffle 14 and an absorbent 16 positioned therebetween. The liquid-permeable cover 12 is designed to contact the body of the wearer and can be constructed of a woven or nonwoven material. The cover 12 can be constructed of natural or synthetic materials and should be easily penetrated by body fluid. Suitable materials include bonded carded webs of polyester, polypropylene, polyethylene, nylon or other heat-bondable fibers. Other polyolefins, such as copolymers of polypropylene and polyethylene, linear low-density polyethylene, finely-perforated film webs and net materials, also work well.

The cover 12 can also be constructed of a thermoplastic film which contains apertures and is flanked on both sides by a nonwoven material. This particular embodiment provides a soft feel against the wearer's thighs while allowing body fluid to rapidly pass therethrough.

The liquid-impermeable baffle 14 is designed to permit the passage of air or vapor out of the absorbent article 10 while blocking the passage of liquids. The baffle 14 can be made from any material having the above-identified properties. A good material is a micro-embossed, polymeric film, such as polyethylene or polypropylene. Bi-component films can also be used. A preferred material is polyethylene film. Most preferably, the baffle 14 will be a polyethylene film having a thickness in the range of about 0.2 mm to about 2.0 mm, preferably about 0.3 mm to about 1.0 mm.

The cover 12 and the baffle 14 can be coextensive and in face to face contact around the periphery of the absorbent 16. The cover 12 and baffle 14 can also be sealed together about their peripheries by use of an adhesive, by heat sealing, by ultrasonics, or by any other process known to those skilled in the art. For example, the cover 12, the baffle 14 and at least a portion of the absorbent 16 can be adhesively joined together and then die cut to have a common periphery. Alternatively, the cover 12 and the baffle 14 can cooperate together to encircle or wrap the absorbent 16.

The absorbent 16 is formed from a first member 18 and a second member 20. The absorbent members 18 or 20 can contain a hydrocolloidal material, commonly referred to as a superabsorbent. It should be noted, however, that the absorbent article 10 works perfectly well without the presence of any superabsorbent material.

The first member 18 is positioned below the cover 12 and can have a length and a width which are approximately equal to the length and width of the absorbent article 10. If the absorbent article 10 is a die cut product, it is possible to stamp out or cut the first member 18, the cover 12 and the baffle 14 in a single operation. However, it should be noted that if one desires to make the first member shorter or narrower than the absorbent article 10, that this is also possible. Preferably, the width of the first member 18 will be equal to the width of the absorbent article 10 such that it spans across the absorbent article 10. If the width of the first member 18 is less than the width of the absorbent article 10, the first member 18 should be aligned along the longitudinal central axis X—X of the absorbent article 10. The reason for this is that such articles are designed to be worn adjacent to the body so that most of the discharged body fluid impinges on the central portion of the cover 12. Therefore, it makes sense to have the first member 18 directly aligned under the region where the body fluid will contact the article 10.

The first member 18 can be a hydrophilic material formed from various types of natural or synthetic fibers, including cellulose fibers, surfactant treated meltblown fibers, wood pulp fibers, regenerated cellulose or cotton fibers, or a blend of pulp and other fibers. Preferably, the first member 18 is formed from a material having a large pore structure and exhibits both wet and dry resiliency to ensure comfort and protection. The first member 18 further has a relatively low wicking capability, especially for menses, when compared to the second member 20. Coform and air-laid fabric are two materials that work well as the first member 18. Coform is an air-formed blend of meltblown fibers and pulp fibers. The formation of such material is disclosed in U.S. Pat. No. 4,100,324 which issued to Anderson et al. This patent is incorporated by reference and made a part hereof. A coform mixture of about 60 percent cellulose fibers with about 40 percent polypropylene meltblown fibers, works well.

An air-laid fabric also works well for the first member 18. A commercially available air-laid fabric is Airtex® 395 sold by James River Corporation located at 500 Day St., P.O. Box 23790, Green Bay, Wis. 54309-3790. Airtex® 395 is 100% virgin softwood with a latex acrylic binder.

The first member 18 can also contain thermoplastic polymers which can be permanently deformed by the application of heat and pressure. Such materials include polypropylene, nylon, polyethylene, polyesters, etc. Typical of such materials are bonded carded webs and spunbond fabrics.

The second member 20 is positioned below at least a portion of the first member 18. The second member 20 has a length which is equal to but preferably less than the length of the absorbent article 10. The second member 20 can be thinner than the first member 18 and has a width which is equal to and preferably less than the width of the first member 18. For an absorbent article 10 having an overall width of between about 2.5 inches to about 4.0 inches (about 63.5 mm to about 101.6 mm) the width of the second member 20 should range from between about 1 to about 2 inches (about 25.4 to about 50.8 mm). Preferably, the width of the second member 20 is between about 1.5 to about 2 inches (about 38.1 to about 50.8 mm). It should be noted that if the absorbent article 10 is a larger article, for example a diaper, the width of the second member could be constructed with a width that is proportionately larger. The reason for making the width of the second member 20 narrower than the width of the absorbent article 10 is that the second member 20 has a greater wicking capability, especially for menses, than any other member of the absorbent article 10. Therefore, fluid in the second member 20 will wick outward along the longitudinal X—X and transverse Y—Y axes faster than the same fluid will wick in the first member 18. If the second member 20 had a width equal to the width of the absorbent article 10, then any fluid that contacted the second member 20 would be wicked outward to the side edges of the absorbent article 10. Side leakage could then occur and the absorbent article 10 would fail to perform it's function, that being, to collect and hold body fluid.

As stated above, the second member 20 has a greater wicking capability than the first member 18. By a greater wicking capability is meant that body fluid contacting the second member 20 will be routed in the x and y directions quicker and more effectively then the same fluid would be routed in those directions in the first member 18 when measured at a time of 5 minutes after initial insult of 3 milliters (ml) of fluid. The x-direction means parallel to the central longitudinal axis X—X and the y-direction means parallel to the central transverse axis Y—Y, both marked on FIG. 1.

Tests were conducted to determine the wicking capabilities of the various materials of different absorbent articles, specifically sanitary napkins. The test procedure determined the wicking capability of the various materials using a dye solution which was dispensed at a flow rate of 3±0.5 ml/30 seconds. Measurements were taken at two different times, at 30 seconds to establish an initial insult and at 5 minutes after initial insult. The equipment and materials needed for the test are as follows:

1. an automated pump capable of dispensing 3±0.5 ml in 30 seconds. An automated Cole Parmer-Masterflex® pump, available from Cole-Parmer Instrument Company, Chicago, Ill. 60648 works well;
2. a 1,000 ml capacity Pyrex graduate with 10 ml graduation;
3. a ring stand—15 inches (381 mm) high;
4. a needle, having a ⅛ inch (3 mm) tip, mounted to the ring stand;
5. Masterflex Tygon tubing, #14, available from Cole-Parmer Instrument Company;
6. 40 ml of a dye solution formed from mixing 16.7 grams of blue dye, No. 1 powder, available from the Warner-Jenkinson Division of Universal Foods Corporation, located at 2526 Baldwin Street, P O Box 14538, St. Louis, Mo. 63178-4538, which has been mixed with 1,000 ml of distilled water;
7. 900 ml of distilled water;
8. a stopwatch, readable to 0.1 second; and
9. a metric ruler.

Before starting the test, 40 ml of the dye solution is gently swirled with 900 ml of distilled water in the 1000 ml capacity pyrex graduate.

The samples to be tested should be conditioned as follows: first, each sample should be removed from a protective package, if the sample is retained in a package. Each sample should then be held at a temperature of 73° F.±1° F. and at a relative humidity of 50%±2% for at least 2 hours. After being conditioned, a 2 by 6 inch (52 mm× 152 mm) specimen is cut from the center of each sample. The longer dimension corresponds to the length of the article from which it is cut.

The test procedure for each specimen is as follows: each 2 by 6 inch specimen is laid on a table with it's body side surface facing up. The tip of the needle is centered over the specimen. The switch which controls the flow of the dye solution from the pump is turned on to allow the dye solution to flow onto the center of the specimen. The stopwatch is started as soon as the dye solution drips onto the specimen. At 30 seconds, the switch to the pump is turned off and the stopwatch is simultaneously stopped. This time period represents what is referred to in the Tables as the "initial insult" and the amount of fluid dispensed should be 3 ml. As quickly as possible, the cover is removed from the specimen. The length and width of the fluid stain on the first and second members, and third member if one is present, are measured with the metric ruler. Each member is carefully peeled apart from the adjacent member in order to measure the fluid stain. This measurement is denoted and recorded and represents the initial insult of the dye solution. All of the members and the cover are then returned to their original position and the stopwatch is started. Five minutes thereafter the stopwatch is stopped. As quickly as possible, the cover is removed from the specimen. The length and width of the fluid stain on the absorbent members, as described above, are measured and recorded. These measurements are denoted and recorded as the "5 minute after insult" reading. This is the final measurement.

The data appearing in Table 1 below was obtained using the above described test procedure. Six, present or past available, commercial sanitary napkins were tested along with four prototypes of the present invention. The four prototypes are labelled as: "Prototype 1"; "Prototype 2"; "Prototype 3" and "Prototype 4". One can see from the data that after 5 minutes from initial insult, the length of the fluid stain in the second absorbent member for each of the four prototypes (129 mm, 152 mm, 100 mm and 135 mm) was much longer than the fluid stain length in any of the commercially available products. The highest value for any of the commercially tested products was 95, see (KUT 2nd member). In summary, the second absorbent member in each of the four prototypes of this invention clearly had a greater wicking capability then the first absorbent member. This feature is not present in any of the commercially available products which were tested. Table 1 also shows that all four prototypes exhibited a large difference in stain length when compared to the fluid stain length at the time of initial insult. For example, Prototype 3 had a difference of 21 mm (100 mm minus 79 mm). The KUT and the NF Maxi were the only two commercially tested products that exhibited such a large difference. The other commercially tested products had a difference of 10 mm or less. This is further proof that the present invention utilizes an absorbent member having a high wicking capability positioned below an absorbent member having a lower wicking capability. Such an arrangement produces unexpected results especially in ultra thin absorbent products which are void of superabsorbent material, provided other conditions are also satisfied.

TABLE 1

WICKING CAPABILITY
(n = 1)
(all measurements in mm)

| Product | Absorbent Member | Composite Size width × length | Square area | stain width after 3 ml insult | stain length after 3 ml insult | stain width 5 minutes after insult | stain length 5 minutes after insult |
| --- | --- | --- | --- | --- | --- | --- | --- |
| AUM | 1-top member | 52 × 152 | 7904 | 45 | 45 | 50 | 50 |
|  | 2-inner member | 52 × 152 | 7904 | 52 | 60 | 52 | 70 |
| SFUP | 1-top member | 52 × 152 | 7904 | 54 | 55 | 54 | 60 |

TABLE 1-continued

WICKING CAPABILITY
(n = 1)
(all measurements in mm)

| Product | Absorbent Member | Composite Size width × length | Square area | stain width after 3 ml insult | stain length after 3 ml insult | stain width 5 minutes after insult | stain length 5 minutes after insult |
|---|---|---|---|---|---|---|---|
| | 2-Sph member | 52 × 152 | 7904 | 54 | 62 | 54 | 66 |
| Prototype 1 | 1-MBX | 32 × 152 | 4864 | 32 | 83 | 32 | 110 |
| | 2-Airtex ® | 52 × 152 | 7904 | 47 | 60 | 49 | 65 |
| | 3-Tissue | 41 × 152 | 6232 | 41 | 98 | 41 | 129 |
| Prototype 2 | 1-Airtex ® | 52 × 152 | 7904 | 50 | 65 | 52 | 67 |
| | 2-Tissue | 41 × 152 | 6232 | 43 | 115 | 43 | 152 |
| Prototype 3 | 1-Airtex ® | 52 × 152 | 7904 | 42 | 42 | 42 | 44 |
| | 2-Tissue | 44 × 152 | 6688 | 44 | 79 | 44 | 100 |
| Prototype 4 | 1-Coform A | 52 × 152 | 7904 | 30 | 30 | 30 | 35 |
| | 2-Tissue | 42 × 152 | 6384 | 42 | 73 | 42 | 135 |
| KUT | 1-Mod. MB | 32 × 152 | 4864 | 32 | 55 | 32 | 55 |
| | 2-Tissue | 52 × 152 | 7904 | 52 | 70 | 52 | 95 |
| | 3-inner member | 32 × 152 | 4864 | 32 | 50 | 32 | 52 |
| NF Maxi | 1-MBX | 52 × 152 | 7904 | 32 | 38 | 32 | 40 |
| | 2-Fluff | 52 × 152 | 7904 | 22 | 24 | 25 | 30 |
| | 3-Emb. Fluff | 52 × 152 | 7904 | 30 | 32 | 40 | 60 |
| NF Thin 1 | 1-Coform B | 52 × 152 | 7904 | 41 | 71 | 42 | 73 |
| | 2-Coform C | 40 × 152 | 6080 | 29 | 32 | 29 | 32 |
| NF Thin 2 | 1-Coform B | 52 × 152 | 7904 | 35 | 57 | 37 | 69 |
| | 2-MBY | 38 × 152 | 5776 | 38 | 51 | 38 | 51 |

Table 2 below shows the ratios of fluid stain length of two adjacent absorbent members in a sanitary napkin for the six tested commercial products and the four prototypes identified in Table 1. The ratio was determined by dividing the fluid stain length in the absorbent member having the greater wicking capability by the fluid stain length in the absorbent member having the lower wicking capability. When the product contained three absorbent members, see Prototype 1; KUT and NF Maxi, fluid stain length for the absorbent member having the highest wicking capability was divided by the fluid stain length of each of the other two members.

The ratios in Table 2 show that for the four prototypes of this invention, the change in stain length 5 minutes after initial insult was 1.7; 2.3; 2.3 and 3.9, respectively. These values are a representation of the relationship of the wicking capability of the greater wicking member to the lower wicking member. A larger value indicates that the difference of wicking is more pronounced between the two members. Another way of stating this is to say that the second member has a wicking capability which is significantly greater than the wicking capability of the first member. This feature enables the second absorbent member to be able to wick the body fluid much more efficiently than the first member. Since the second member is positioned below at least a portion of the first member, the body fluid is drawn into the second member and wicked throughout it's entire surface very quickly. The fluid is then transferred back to the first member over a much larger surface area.

One will notice that in Table 2, the commercial products contained ratios between 1.1 and 2.3. However, in the "NF Thin 1" product, the greater wicking member (coform B) is wider than and positioned above the lower wicking member (coform C). In the KUT product, the greater wicking member (tissue) is wider than both of the lower wicking members (Mod. MB and inner member). This construction is opposite to the construction of the present invention and could lead to premature side leakage. In those commercial products where the width of the high wicking member was equal to or less than the width of the low wicking member, the values were 2.0 or less. Such values indicate that there is less of a difference in wicking capability between the absorbent members.

TABLE 2

RATIOS OF STAIN LENGTH
(n = 1)

| Product | Ratio of Members | stain length ratio after 3 ml insult | stain length ratio 5 min. after insult |
|---|---|---|---|
| AUM | Member (2):Member (1) | 1.3 | 1.4 |
| SFUP | Member (2):Member (1) | 1.1 | 1.1 |
| Prototype 1 | Member (1):Member (2) | 1.4 | 1.7 |
| | Member (3):Member (2) | 1.6 | 2.0 |
| Prototype 2 | Member (2):Member (1) | 1.8 | 2.3 |
| Prototype 3 | Member (2):Member (1) | 1.9 | 2.3 |
| Prototype 4 | Member (2):Member (1) | 2.4 | 3.9 |
| KUT | Member (2):Member (1) | 1.3 | 1.7 |
| | Member (2):Member (3) | 1.4 | 1.8 |
| MF Maxi | Member (3):Member (1) | 0.8 | 1.5 |
| | Member (3):Member (2) | 1.3 | 2.0 |
| NF Thin 1 | Member (1):Member (2) | 1.4 | 2.3 |
| NF Thin 2 | Member (1):Member (2) | 1.1 | 1.35 |

Note: The products and members in Table 2 correspond to the products and members identified in Table 1.

In Table 3, the wicking capability in terms of stain length of the six commercial products and the four prototypes described in Tables 1 and 2 are given. The fluid stain length after the initial "3 ml" insult (at 30 seconds) and "5 minutes after initial insult" are listed. The values in the right hand column "Stain length 5 minutes after insult" clearly show that for the four prototypes, the fluid stain length has progressed more than 76 mm, (129 mm, 152×mm, 100 mm and 135 mm, respectively). In fact, the fluid stain length exceeded 99 mm for all four prototypes. In the commercial products, the fluid stain lengths were less than 76 mm in every product except KUT which measured 95 mm. These fluid stain lengths further support the fact that the second absorbent member in this invention has a greater wicking capability than the first member. The combination of ratio of fluid stain length of the high wicking member divided by the fluid stain length of the low wicking member being greater than 1.7 along with the fluid stain being at least 76 mm, and preferably at least 99 mm in the high wicking member produces an unexpected result that enables the present invention to function much better than any of the tested products. It should be noted that the time period to determine the ratio is at 5 minutes after initial insult of 3 ml.

The NF Maxi commercial product has a fluid stain length of 60 mm in the high wicking member, well below 76 mm. Therefore, even though the wicking ratio is 2.0, the fluid stain length of the high wicking member is low, showing that the fluid is not being well distributed along the high wicking member, and is outside the present invention.

TABLE 3

WICKING CAPABILITY - STAIN LENGTH
Change in stain length on absorbent members
(n = 1)
(all measurements in mm)

| Product | Absorbent Member | Initial Sample Length 152 mm stain length after 3 ml insult | stain length 5 minutes after insult |
| --- | --- | --- | --- |
| AUM | 1st member | 45 | 50 |
|  | 2nd member | 60 | 70 |
| SFUP | 1st member | 55 | 60 |
|  | 2nd member | 62 | 66 |
| Prototype 1 | 1st member | 83 | 110 |
|  | 2nd member | 60 | 65 |
|  | 3rd member | 98 | 129 |
| Prototype 2 | 1st member | 65 | 67 |
|  | 2nd member | 115 | 152 |
| Prototype 3 | 1st member | 42 | 44 |
|  | 2nd member | 79 | 100 |
| Prototype 4 | 1st member | 30 | 35 |
|  | 2nd member | 73 | 135 |
| KUT | 1st member | 55 | 55 |
|  | 2nd member | 70 | 95 |
|  | 3rd member | 50 | 52 |
| NF Maxi | 1st member | 38 | 40 |
|  | 2nd member | 24 | 30 |
|  | 3rd member | 32 | 60 |
| NF Thin 1 | 1st member | 71 | 73 |
|  | 2nd member | 32 | 32 |
| NF Thin 2 | 1st member | 57 | 69 |
|  | 2nd member | 51 | 51 |

Note: The products and members in Table 3 correspond to the products and members identified in Table 1. Some swelling occurred in some of the composite members resulting in stain sizes slightly larger than the cut size.

The second member 20 is preferably constructed of tissue. The tissue can be made from softwood and/or hardwood fibers and can be creped, wet pressed or through-air dried. More than one layer can be used with the layers separate and distinct or the layers can be formed by folding a single sheet of tissue one or more times. It has been found that two or more layers work well. Preferably, the second member 20 is an E-folded tissue having three or more connected layers. For an absorbent article 10 having an overall length of about 7 inches (about 177.8 mm) or more, the tissue can have a length of about 6 inches to about 7 inches (about 152.4 mm to about 177.8 mm). The tissue facilitates fluid wicking throughout the entire surface area of the second member 20 and fluid dispersement into the first member 18. The tissue can increase the rate at which fluid can be drawn in and retained by the absorbent 16 by as much as approximately 25 percent over a conventional pulp absorbent.

The density of the tissue should also be greater than the density of the first member 18. The density of the first member 18 should be between about 3 to about 6 pounds per cubic foot, preferably between about 4 to about 5 pounds per cubic foot. Thus, the density of the second member 20 should be at least about 4 pounds per cubic foot or greater, and preferably, about 6 pounds per cubic foot. More preferably, the density of the second member 20 should be about 7 pounds per cubic foot.

Figure 3:
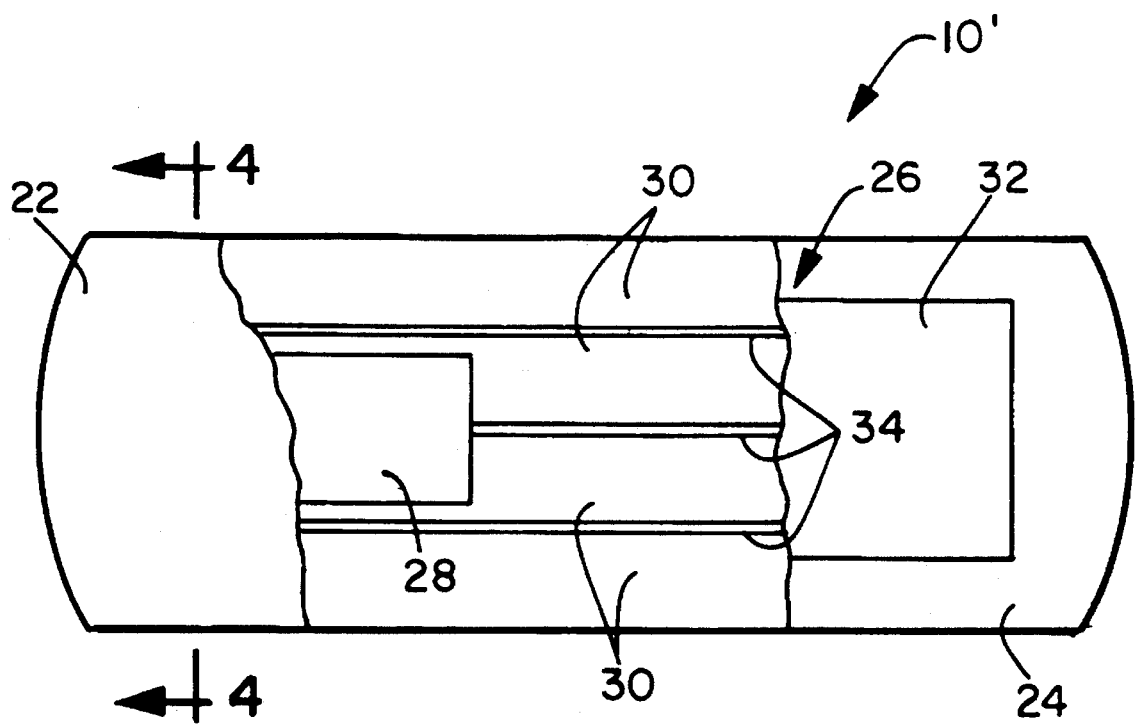
FIG. 3 is a top view of an alternative embodiment of an absorbent article having a transfer layer and three longitudinal slits formed in the first member.
Figure 4:
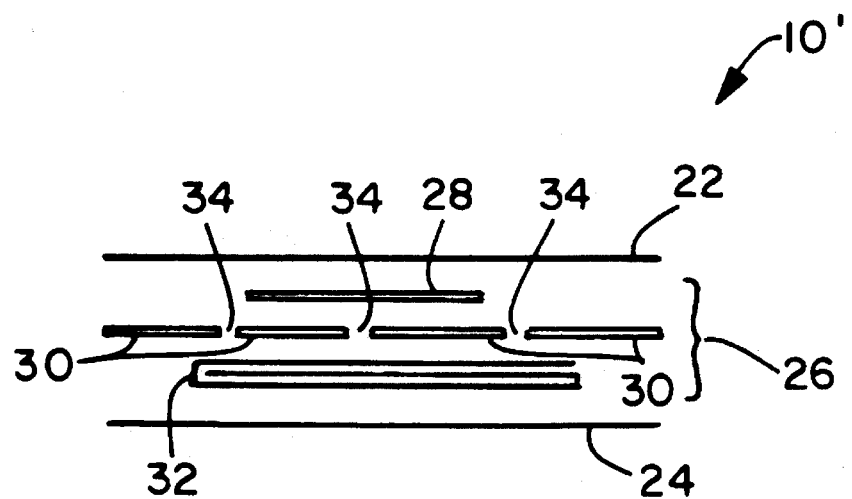
FIG. 4 is a cross-sectional view of FIG. 1 taken along line 4—4.

Referring to FIGS. 3 and 4, an alternative embodiment of an absorbent article 10' is shown. The absorbent article 10' includes a liquid-permeable cover 22, a liquid-impermeable baffle 24, and an absorbent 26. The absorbent 26 includes a transfer layer 28, a first absorbent member 30 and a second absorbent member 32. The transfer layer 28 is positioned between the cover 22 and the first member 30 and is aligned along a central longitudinal axis X—X of the absorbent article 10'. The transfer layer 28 can be a nonwoven polypropylene spunbond web or other material having similar properties.

The transfer layer 28 can be in the shape of a rectangular strip, having a length equal to or less than the overall length of the absorbent article 10', and a width less than the width of the absorbent article 10'. A length of between about 6 to about 12 inches (about 152 mm to about 304 mm) and a width of between about 0.5 to about 2 inches (about 12 mm to about 25.4 mm) works well for a sanitary napkin. Preferably, the transfer layer 28 has a length approximately equal to the length of the absorbent article 10', and a width of between about 1 to about 1.5 inches (about 25.4 mm to about 38.1 mm), most preferably about 1.25 inches (about 31.75 mm).

The transfer layer 28 is capable of passing body fluid downward from the cover 22 to the absorbent 26. The transfer layer 28 provides a pre-use visual signal to the user that the primary absorbent portion of the article 10" is situated along the central longitudinal axis X—X of the absorbent article 10'.

The absorbent article 10' is also different from the embodiment depicted in FIGS. 1 and 2 in that the first member 30 contains one or more longitudinal gaps 34. The gaps 34 can vary in length and width and can be formed by making cuts or slits in the first member 30 or by forming the first member 30 out of separate strips which are aligned side by side in a horizontal plane. Each gap 34 provides an unobstructive pathway for body fluid, especially menses, to flow from the cover 22 and/or the transfer layer 28 down into the second member 32. The gaps 34 allow the absorbent article 10" to bend and fold so as to stay in intimate contact with the body of the user. The gaps 34 also allow rapid penetration of the body fluid into the lower portion of the absorbent article 10' and this is highly desirable in keeping the cover 22 dry. The gaps 34 are especially useful in sanitary products were menses is being absorbed because menses is a very viscous fluid which does not flow easily through fibrous materials.

The second member 32 serves the same purpose as the second member 20, described in FIG. 1. The second member 32 is depicted as having a width larger than the transfer layer 28 but narrower than the first member 30. Again, the reason for this is that the second member 32 has a greater wicking capability than the first member 30. By sizing the width of the second member 32 to be less than the first member 30, the fluid will not migrate to the side edges of the absorbent article 10' until the fluid has filled the second member 32. This delays the possibility of side leakage.

Figure 5:
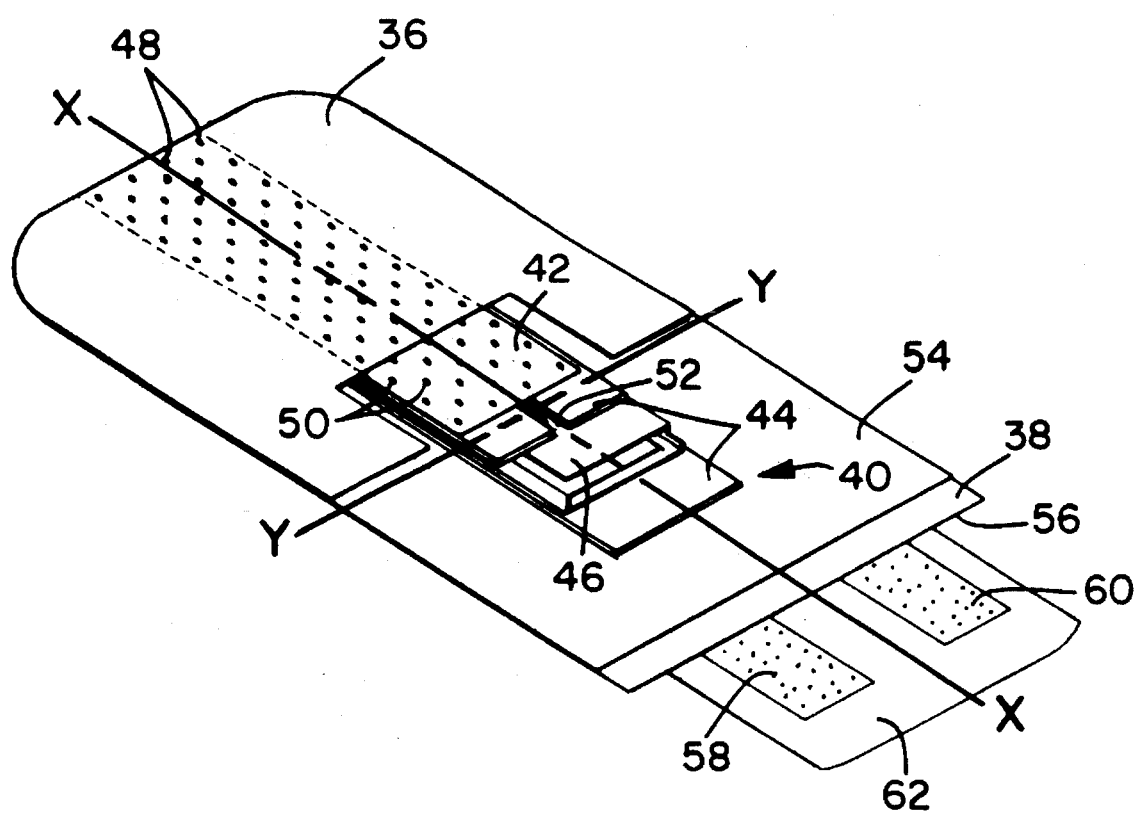
FIG. 5 is a perspective view of another embodiment of an absorbent article having a transfer layer and the second member enclosed by the first member with a slit in the top layer of the first member.

Referring to FIG. 5, a third embodiment of an absorbent article 10" is shown having a liquid-permeable cover 36, a liquid-impermeable baffle 38 and an absorbent 40. The cover 36 and the baffle 38 are sealed together about the periphery of the absorbent article 10". The absorbent 40 includes a transfer layer 42, a first member 44 and a second member 46. All three members 42, 44 and 46 are vertically arranged and have the properties discussed above in reference to FIGS. 1–4. However, in this embodiment, a plurality of apertures 48 and 50 are formed completely through both the cover 36 and the transfer layer 42, respectively. The apertures 48 and 50 facilitate movement of body fluid down into the absorbent 40. Some or all of the apertures 48 formed in the cover 36 and the apertures 50 formed in the transfer layer 42 can be axially aligned so as to rapidly allow the body fluid to penetrate down into the absorbent 40. The size, shape, diameter and number of apertures 48 and 50 can vary to suit one's particular needs. The apertures 48 and 50 can be uniformly or randomly arranged throughout all or a portion of the cover 36 and the transfer layer 42. As shown, the apertures 48 are arranged in a narrow strip aligned along the central longitudinal axis X—X of the absorbent article 10". The width of the apertured section of the cover 36 can be equal to the width of the transfer layer 42. Preferably, the entire surface of the transfer layer 42 will be apertured.

In FIG. 5, one will notice that the first member 44 consists of two layers, one above and one below the second member 46. The top layer of the first member 44 contains a single gap 52 axially aligned with the central longitudinal axis X—X. The gap 52 can be formed by cutting or slitting the top layer of the first member 44 or by constructing the first member 44 from two separate strips of material that are aligned parallel to one another and slightly spaced apart. The gap 52, along with the apertures 48 and 50, provide a plurality of unobstructive pathways from the cover 36 to the second member 46. It should be noted that if only one gap is present, it should be aligned along the central longitudinal axis X—X for then it will be vertically situated between the central portion of the cover 36, where the fluid will enter the absorbent article 10", and the center of the second member 46. The center of the second member 46 will allow the fluid to be quickly wicked to the periphery of the tissue.

In FIG. 5, the combined width of the two strips forming the first member 44 is equal to the width of the second member 46. From a manufacturing prospective, it may be advantageous to make the first and second members, 44 and 46 respectively, of equal size for this could facilitate vertical alignment of one member relative to the other member.

The absorbent article 10" also contains a wet resilient layer 54, which is positioned between the bottom layer of the first member 44 and the liquid-impermeable baffle 38. The wet resilient layer 54 can be a closed cell, polyethylene foam presently commercially sold by Sealed Air Corporation, 7110 Santa Fe Drive, Hodgkins, Ill. 60525. The foam is sold as Cell-Aire®, CA-30 having a thickness of about 1/32 of an inch (about 0.8 mm), with a density of 1.2 pounds per cubic foot, a width of 60 inches, and on rolls having a linear length of 2000 feet (615 meters). Another polyethylene foam that is also suitable for the wet resilient layer 54, is sold by Ametek Microfoam Division, Brandwine Four Building, Routes 1 and 202, Chadds Ford, Pa. 19317.

The wet resilient layer 54 serves to resist bunching and twisting of the absorbent article 10" during use. By wet resilient is meant that the layer 54 is resilient even when wetted by body fluid. The wet resilient layer 54 has a length and a width which can be coterminous with the length and width of the cover 36 and/or the baffle 38. The wet resilient layer 54 should have a width equal to or greater than the width of the absorbent 40, and a length equal to, and preferably, greater than the length of the absorbent 40. The wet resilient layer 54 resists bunching and twisting of the absorbent article 10" and therefore cooperates with the gap 52 in keeping the absorbent article 10" in intimate contact with the wearer's body.

Physically attached to an exterior surface 56 of the baffle 38, are two longitudinally extending strips of garment attachment adhesive 58 and 60. It should be noted that one wide strip, three or more narrow strips, or a spray pattern of adhesive can also be used. The garment attachment adhesive is commercially available from National Starch and Chemical Company, located at 10 Finderne Ave., Bridgewater, N.J. 08807. The garment adhesive strips 58 and 60 are used to secure the absorbent article 10" to the inside of the crotch portion of an undergarment, when the absorbent article 10" is a catamenial product. If the absorbent article 10" is a diaper or a training pant, the garment adhesive strip 58 and 60 may not be needed. The garment adhesive strips 58 and 60 serve to properly align the absorbent article 10" over the vaginal opening.

A releasable peel strip 62 is attached to the garment adhesive strips 58 and 60 and serves to prevent the adhesive from becoming contaminated prior to attachment to an undergarment. The peel strip 62 can be a white Kraft paper, coated on one side, so that it can be released from a hot melt adhesive, such as the garment adhesive strips 58 and 60. The peel strip 62 is designed to be removed by the ultimate consumer just prior to placement of the absorbent article 10" in the undergarment.

While the invention has been described in conjunction with several specific embodiments, it is to be understood that many other alternatives, modifications and variations will be apparent to those skilled in the art in light of the aforegoing description.

Accordingly, this invention is intended to embrace all such alternatives, modifications and variations which fall within the spirit and scope of the appended claims.

I claim:

1. An absorbent article comprising an absorbent including a first member and a second member, said first member being positioned vertically above said second member and in contact therewith, said first member being a blend of polymer and pulp fibers, said first and second members each having a predetermined width, with the width of said first member being greater than the width of said second member, and said second member having a greater wicking capability for approximately 3 milliliters of dyed distilled water than said first member, said wicking capability being expressed as a ratio of length of a fluid stain in said second member to length of a fluid stain in said first member, said ratio being at least 1.7 when the length of said fluid stain in said second member is at least 76 mm.

2. The absorbent article of claim 1 wherein said article has a thickness of less than about 5 mm.

3. The absorbent article of claim 1 wherein said second member is a through-air dried, creped tissue.

4. The absorbent article of claim 1 wherein said second member is tissue which is E-folded to form at least three connected layers and said tissue has a width of between about 1.0 to about 2.0 inches.

5. The absorbent article of claim 1 wherein said second member has a width of between about 1.5 to about 2.0 inches.

6. The absorbent article of claim 1 wherein said second member is constructed of at least two layers.

7. An absorbent article comprising:

a) a liquid-permeable cover;

b) a liquid-impermeable baffle;

c) an absorbent enclosed by said cover and said baffle, said absorbent including a first member and a second member, said first member being positioned vertically above said second member and in contact therewith, said first member being a blend of polymer and pulp fibers, said first and second members each having a predetermined width, with the width of said first member being equal to the width of said second member, and said second member having a greater wicking capability for approximately 3 milliliters of dyed distilled water than said first member, said wicking capability being expressed as a ratio of length of a fluid stain in said second member to length of a fluid stain length in said first member, said ratio being at least 1.7 when the length of said fluid stain in said second member is at least 76 mm.

8. The absorbent article of claim 7 wherein said second member is a through-air dried, creped tissue.

9. The absorbent article of claim 7 wherein said second member is tissue which is E-folded to form at least three connected layers and said tissue has a width of between about 1.0 to about 2.0 inches.

10. The absorbent article of claim 7 wherein said second member has a width of between about 1.5 to about 2.0 inches.

11. The absorbent article of claim 7 wherein said second member is constructed of at least two layers.

12. The absorbent article of claim 7 wherein said article has a thickness of less than about 5 mm.

13. An absorbent article comprising:

a) a liquid-permeable cover;

b) a liquid-impermeable baffle;

c) an absorbent enclosed by said cover and said baffle, said absorbent including a first member and a second member, said first member being positioned vertically above said second member and in contact therewith, said first member having a basis weight of about 100 grams per square meter, Said first and second members each having a predetermined width, with the width of said first member being greater than the width of said second member, and said second member having a greater wicking capability for approximately 3 milliliters of dyed distilled water than said first member, said wicking capability being express as a ratio of length of a fluid stain in said second member to length of a fluid stain length in said first member, said ratio being at least 1.7 when the length of said fluid stain in said second member is at least 76 mm.

14. The absorbent article of claim 13 wherein said second member is a through-air dried, creped tissue.

15. The absorbent article of claim 13 wherein said second member is tissue which is E-folded to form at least three connected layers and said tissue has a width of between about 1.0 to about 2.0 inches.

16. The absorbent article of claim 13 wherein said second member has a width of between about 1.5 to about 2.0 inches.

17. The absorbent article of claim 13 wherein said article has a thickness of less than about 5 mm.

18. An absorbent article comprising:

a) a liquid-permeable cover;

b) a liquid-impermeable baffle;

c) an absorbent enclosed by said cover and said baffle, said absorbent having a predetermined width and including a first member and a second member, said first member being positioned vertically above said second member and in contact therewith, said first member being a blend of polymer and pulp fibers and having a basis weight of about 100 grams per square meter, said first member having a width which spans the width of said absorbent article, and said second member being an E-folded tissue having at least three connected layers and having a greater wicking capability for approximately 3 milliliters of dyed distilled water than said first member.

19. The absorbent article of claim 18 wherein said second member is a through-air dried, creped tissue.

20. The absorbent article of claim 18 wherein said first member is coform.

21. The absorbent article of claim 18 wherein said first member is an air-laid fabric.

22. The absorbent article of claim 18 wherein a transfer layer is positioned between said cover and said first member.

23. The absorbent article of claim 18 wherein said article has a thickness of less than about 5 mm.

24. The absorbent article of claim 18 wherein said first member has at least one longitudinal slit formed therein which extends lengthwise along a portion thereof.

25. The absorbent article of claim 24 wherein said first member has a plurality of slits formed therein which extend lengthwise along a portion thereof.

26. An absorbent article comprising:

a) a liquid-permeable cover;

b) a liquid-impermeable baffle;

c) an absorbent enclosed by said cover and said baffle, said absorbent including a first member and a second member, said first member being positioned vertically above said second member and in contract therewith, Said first member being a blend of polymer and pulp fibers and having a basis weight of about 100 grams per square meter, said first member including at least two horizontally aligned and spaced apart strips which have at least one longitudinal gap formed therebetween, said first member having a predetermined width which includes the width of said strips and said longitudinal gap, and said second member having a predetermined width, said width of said first member being greater than the width of said second member, said second member being an E-folded tissue having at least three layers and having a greater wicking capability for approximately 3 milliliters of dyed distilled water than said first member, said wicking capability being expressed as a ratio of length of a fluid stain in said second member to length of a fluid stain length in said first member, said ratio being at least 2.3 when the length of said fluid stain in said second member is at least 99 mm.

27. The absorbent article of claim 26 wherein a transfer layer is positioned between said cover and said first member and said transfer layer is darker in color than said first member, said darker color providing a pre-use visual signal to the user of where a majority of the fluid should be retained.

28. The absorbent article of claim 26 wherein said second member is a through-air dried, creped tissue.

29. The absorbent article of claim 26 wherein said second member is tissue which is E-folded to form at least three connected layers and said tissue has a width of between about 1.0 to about 2.0 inches.

30. The absorbent article of claim 26 wherein said article has a thickness of less than about 5 mm.

* * * * *